US00PP17234P3

(12) United States Plant Patent
Stemkens

(10) Patent No.: US PP17,234 P3
(45) Date of Patent: Nov. 28, 2006

(54) ***SUTERA* PLANT NAMED 'SUTCABL'**

(50) Latin Name: *Sutera diffusa*
Varietal Denomination: Sutcabl

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 206 days.

(21) Appl. No.: 11/002,510

(22) Filed:
Dec. 2, 2004

(65) Prior Publication Data

US 2006/0123522 P1 Jun. 8, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP13,181 P2 * 11/2002 Brown ..... Plt./263
PP15,254 P2 * 10/2004 Stemkens ..... Plt./263

OTHER PUBLICATIONS

UPOV ROM GTITM Computer Database, GTI Jouve Retrieval Software 2005/03 Citations for 'Sutcabl'.*

* cited by examiner

*Primary Examiner*—Kent Bell
*Assistant Examiner*—W C Haas
(74) *Attorney, Agent, or Firm*—Bruce Vrana

(57) ABSTRACT

A new and distinct variety of *Sutera* plant particularly distinguished by its larger blue flowers than other *Sutera* plants, earlier to flower, by thick stems and a growing habit that is compact.

1 Drawing Sheet

Latin name of the genus and species of the plant claimed: *Sutera diffusa.*

Varietal denomination: 'Sutcabl'.

BACKGROUND OF THE NEW PLANT

The present invention comprises a new distinct cultivar of *Sutera,* botanically known as *Sutera diffusa.*

The new cultivar is propagated from cuttings resulting from the cross of 'B21' and 'B23'. 'B21' is a lavender blue flowering *Sutera* having a spreading, trailing habit. 'B21' is not commercially available and is not known by any synonyms. 'B23' is a white flowering *Sutera* having a larger than normal flower. 'B23' is not commercially available and is not known by any synonyms. Neither 'B21' or 'B23' has been patented.

As a result of this cross the present cultivar was created in 2000 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty is firmly fixed.

This new *Sutera* plant is an annual in most climatical zones in the US, only in zones 9 and 10 it is a perennial plant.

'Sutcabl' is coming from the same cross as the variety 'Sutharis', U.S. Plant Pat. No. 15,254, from which it differs in having a blue color instead of a lavender color and having smaller flowers. Also 'Sutcatrbl' (U.S. Plant patent application Ser. No. 11/002,472) is from the same cross.

SUMMARY OF THE INVENTION

It was found that the cultivar of the present invention:

a) exhibits blue flowers;

b) has thick stems; and c) exhibits a compact habit growth

DESCRIPTION OF THE DRAWING

This new *Sutera* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Sutera.* The data that define these characteristics were collected from asexual reproductions carried out in Enkhuizen, Netherlands. The plant history was taken on 15 week old plants, blossomed under natural light in a greenhouse and grown in a 11 cm container. Colour readings were taken in the greenhouse under ambient light. Colour references are primarily to The R.H.S. Colour Chart of The Royal Horticultural Society of London.

TABLE 1

Differences between the new cultivar 'Sutcabl', its parents and a similar cultivar

| | 'Sutcabl' | 'B21' | 'B23' | 'Blue Showers' |
|---|---|---|---|---|
| Flower color | Deep Blue | Deep blue | White | Blue |
| Stem thickness | Thick | Medium | Thick | Thin |
| Plant habit | Compact | Trailing | Compact | Trailing |
| Flower size | Medium | Big | Small | Small |

The commercial name of the most resembling variety is 'Blue Showers'. The patented name of this variety is 'Bacoble' and its U.S. Plant Pat. No. is PP 13,181.

The plant:
Classification — Botanical: *Sutera diffusa.*
Parentage:
*Female parent.*—A seedling named 'B21' is one of our seedlings from out B-generation of plants bred in 1999.
*Pollen parent.*—A seeding named 'B23' is one of our seedings from our B-generation of plants bred in 1999.
Growth habit: Compact.
Plant height: 10 to 15 cm.
Spreading area of plant: 22 to 28 cm.
Growth rate: Rapid growing.
Strength: Good.
Branching habit: Short internodes and on each knot more than two appearing shoots give a plant that is more branched than normal.
Blooming period: From May until November.
The stem:
Diameter: 2 to 3 mm.
Shape: Cylindrical.
Anthocyanin pigmentation: Absent.
Color of the stem: 137A.
Length of internode: 8 to 20 mm, depending on the light where the plant is propagated.
Pubescence: Sparse.
The foliage:
Phyllotaxis: Opposite.
Shape of blade: Broadly ovate.
Shape of the blade apex: Rounded.
Shape of the blade base: Shortly attenuate.
Leaf margin: Crenate. Venation: Pinnate.
Texture:
*Upper surface.*—Smooth, glabrous.
*Lower surface.*—Slightly pubescent.
Length: 12 to 22 mm.
Width: 15 to 23 mm.
Thickness: 1 to 2 mm.
Depth of incision: 1 mm.
Color:
*Upper side.*—137A.
*Lower side.*—137B.
Length of petiole: 1 mm.
Diameter of petiole: 1 mm.
Color of petiole: 137A.
Fragrance: Musk.
The bud:
Pedicel length: 8 to 14 mm, depending on season.
Pedicel diameter: 1 mm.
Pedicel color: 137B.
Pedicel angle: About 60 degrees from the stem.
Bud size:
*Diameter.*—1 mm.
*Length.*—4 to 8 mm.
Bud shape: Obovate.
Bud color: 85B.
Sepals:
*Color.*—137D to 137B.
*Number.*—5.
*Shape.*—Erect calyx.
*Size.*—1 mm.
The flower:
Flower diameter: 10 to 15 mm.
Flower tube length: 4 to 8 mm.
Throat diameter, distal end: 2 to 3 mm.
Tube diameter, proximal end: 1.5 to 2.5 mm.
Form: Salverform.
Symmetry: Radial symmetric.
Type: Solitary, axillary.
Color:
*Upper surface.*—Between 92A and 92B.
*Lower surface.*—92C.
Corolla tube: Cylindrical.
Corolla tube color: 8B.
Overlapping of petals: Separate.
No. of petals: 5.
Shape of the petals: Gamopetalous, grown together at the base of the petal, forming a corolla.
Petal lobe: —
*Length.*—4 to 6 mm.
*Width.*—2 to 4 mm.
*Shape.*—Spatulate.
*Apex.*—Rounded.
*Margin.*—Entire.
*Texture.*—Smooth.
Shape of sepals: Gamopetalous, grown together at the base of the sepal.
Calyx:
*Length.*—6 to 8 mm.
*Diameter.*—3 mm.
*Shape.*—Narrow, linear.
*Margin.*—Entire.
Texture of the calyx:
*Upper surface.*—Pubescent.
*Lower surface.*—Pubescent.
Color of the calyx:
*Upper surface.*—137B.
*Lower surface.*—137C.
Anthocyanin pigmentation of calyx limb: Absent.
Flower fragrance: No fragrance detected.
Lastingness of one flower: Flowers stay open 8 to 10 days.
Reproductive organs:
Number of reproductive organs: 1 pistil, 4 stamens.
Pollen production: Very low.
Stigma color: Light green 138D.
Stamen color: Yellow 13A. Stamen arrangement: Didynamous.
Stamen type: Basifixed.
Dehiscence of stamens: Extrorse.
Ovary position: Ovary superior, flower hypogynous.
Style shape: Style terete.
Style length: 5 mm.
Pistil length: 8 mm.
Seeds: Only a few seeds are formed, almost sterile plant. Few seeds that occur are light yellow 13C, small, round, diameter approximately 0.1 mm.
Roots:
Type of roots: Fibrous, color 155A.
Physiological and ecological characteristics: No exceptional physiological and ecological differences with other cultivars of *Sutera diffusa* are observed.
Propagation: Propagation is done by axillary cuttings. Tips of stems are used, which take 6 days to initiate roots and 12 days to develop roots.

What is claimed is:

1. A new and distinct variety of *Sutera* plant named 'Sutcabl', substantially as illustrated and described herein.

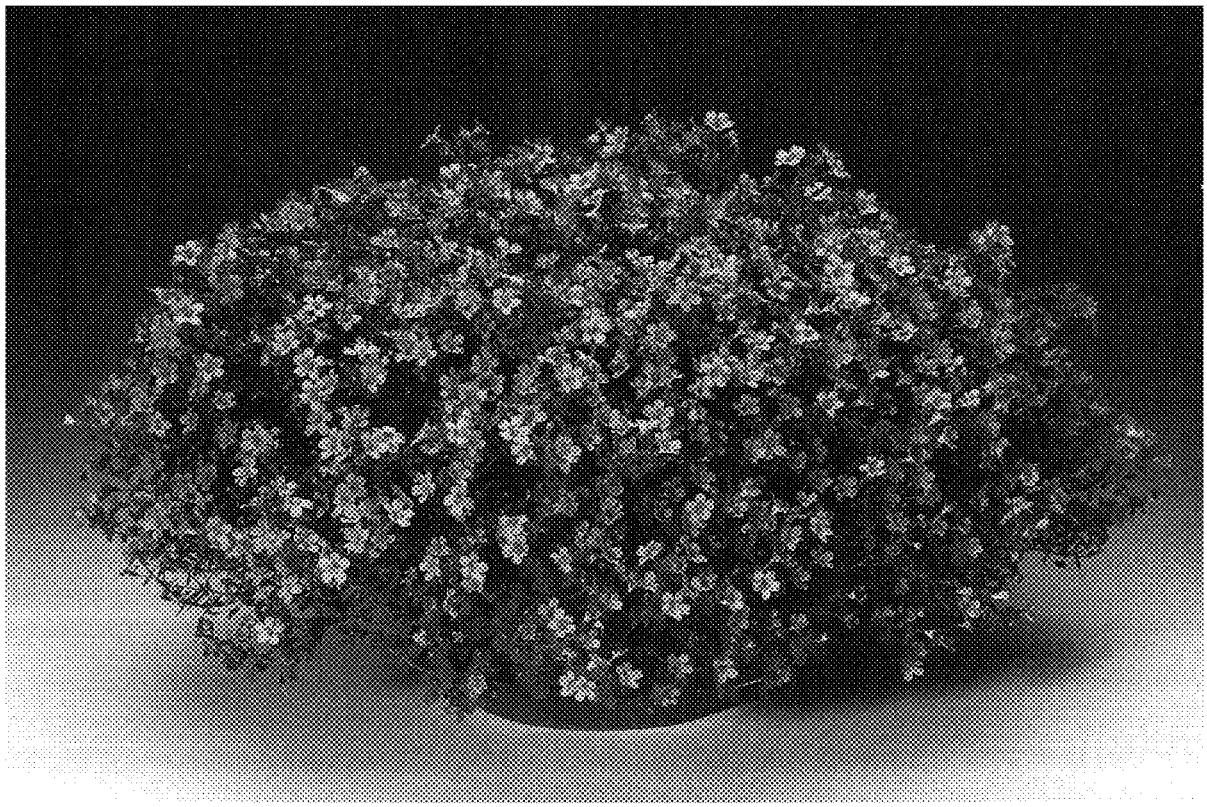

* * * * *